United States Patent
Arumugham et al.

(10) Patent No.: US 10,526,268 B2
(45) Date of Patent: Jan. 7, 2020

(54) SYSTEMS AND METHODS FOR PRODUCING SYNTHETIC HYPERICIN

(71) Applicant: Soligenix, Inc., Princeton, NJ (US)

(72) Inventors: Rasappa Arumugham, Princeton, NJ (US); Christopher Schaber, Princeton, NJ (US); Holger Rauter, Flieden (DE); Silvia Werner, Kahl (DE)

(73) Assignee: Soligenix, Inc., Princeton, NJ (US)

( * ) Notice: Subject to any disclaimer, the term of this patent is extended or adjusted under 35 U.S.C. 154(b) by 0 days.

(21) Appl. No.: 16/107,047

(22) Filed: Aug. 21, 2018

(65) Prior Publication Data

US 2019/0135724 A1     May 9, 2019

Related U.S. Application Data

(62) Division of application No. 15/057,458, filed on Mar. 1, 2016, now Pat. No. 10,053,413.

(51) Int. Cl.
*C07C 46/10* (2006.01)

(52) U.S. Cl.
CPC .......... *C07C 46/10* (2013.01); *C07C 2603/54* (2017.05)

(58) Field of Classification Search
CPC .............................. C07C 46/10; C07C 2603/54
See application file for complete search history.

(56) References Cited

U.S. PATENT DOCUMENTS

| | | |
|---|---|---|
| 5,543,016 A | 8/1996 | Fehlner et al. |
| 8,629,302 B2 | 1/2014 | Tobia et al. |
| 2012/0245392 A1 | 9/2012 | Tobia et al. |
| 2013/0211371 A1 | 8/2013 | Tobia et al. |

FOREIGN PATENT DOCUMENTS

CA        2029993 A1 *  5/1991  ............. C07C 46/00

OTHER PUBLICATIONS

Zaragoza Dorwald, Side Reactions in Organic Synthesis, 2005, WILEY-VCH Verlag GmbH & Co. KGaA, Weinheim, Preface. p. IX. (Year: 2005).*
Kapinus et al (Monatshefte für Chemie, Spectroscopic Investigation of the Molecular Structure of Hypericin and its Salts, 1999, 130 pp. 623-635. (Year: 1999).*
Karioti et al., "Rapid and efficient purification of naphthodianthrones from St. John's wort extract by using liquid-liquid extraction and SEC." J. Sep. Sci. 2009, 32, 1374-1382.
Kapinus et al., "Spectroscopic investigation of the molecular structure of hypericin and its salts." Monatshette fuer Chemie, 1999, vol. 130, 623-635.

* cited by examiner

*Primary Examiner* — Paul A Zucker
(74) *Attorney, Agent, or Firm* — Lewis Kohn & Walker LLP; David M. Kohn; Kari Moyer-Henry

(57) ABSTRACT

Improved systems and methods for producing synthetic hypericin at high volume and high purity. In particular, systems and methods of preparing a purified synthetic hypericin resulting from irradiation, wherein the irradiation step is performed in a continuous flow micro-reactor. The process of manufacturing purified synthetic hypericin results in the synthetic yield of 30-100% of the dry product.

13 Claims, 2 Drawing Sheets

SYSTEMS AND METHODS FOR PRODUCING SYNTHETIC HYPERICIN

RELATED APPLICATIONS

This application claims priority from U.S. patent application Ser. No. 15/057,458 filed on Mar. 1, 2016, now U.S. Pat. No. 10,053,413, the contents of which are hereby incorporated by reference herein.

FIELD OF THE INVENTION

The present invention relates to systems and methods for producing synthetic hypericin. Particularly, the present invention relates to improved systems and methods for producing synthetic hypericin at high volume and high purity.

BACKGROUND OF THE INVENTION

Hypericin is a natural compound found in stems and petals of plants of the genus *Hypericum*. Within this genus are eight families and 43 species, including the common St. John's wort plant, *Hypericum perforatum*. Hypericin is the principle phototoxic agent in St. John's wort. The chemical name is 1,3,4,6,8,13-hexahydroxy-10,11-dimethylphenanthro[1,10,9,8-opqra]perylene-7,14-dione (other names: 4,5, 7,4',5',7' hexahydroxy-2,2'-dimethyl-meso naphthodianthrone; Phenanthro[1,10,9,8-opqra]perylene-7,14-dione, 1,3,4,6,8,13-hexahydroxy-10,11-dimethyl-), a compound composed of eight conjugated rings containing six hydroxyl groups, two carbonyl and two methyl groups in a symmetric pattern when inverted about a central axis.

Hypericin is one of the most important phenanthoperylene quinones extracted mainly from plants of the genus *Hypericum*. Widespread attention to the antiviral and anti-tumor properties of hypericin has spurred investigations of the chemical synthesis and biosynthesis of this unique compound. However, the synthetic strategies are challenging for organic and biological chemists.

In the past, isolation of hypericin from plants was not practical on a large scale because it requires a lengthy procedure involving extraction with large columns of solvents and cumbersome chromatographic separations on silica gel columns. The main difficulty in obtaining hypericin in a pure state from the plant material resides in its separation from the accompanying pseudohypericin. This necessitates the aforementioned chromatography with the elution of a large number of fractions, only a few of which contain the pure desired material. The concentration of hypericin in the plants is very low, not more than 0.3% based on the dry plant material.

U.S. Pat. No. 8,629,302 B2 issued to Tobia et al discloses a method for making hypericin comprising steps starting from emodine to emodine anthrone which is then dimerized to protohypericin salt and then photoconverted to hypericin. However, the method requires re-circulation of protohypericin solution to effectively convert to hypericin making the process unscalable. Furthermore, the purified hypericin was hygroscopic, adsorbing moisture over storage time and found to be in a mixture of salt and acid form. Presently, there is a need for novel and highly effective systems and methods for producing synthetic hypericin having a well-defined compositional matter on a large scale.

SUMMARY OF THE INVENTION

An object of the present invention provides a novel, purified synthetic hypericin.

Yet another object of the present invention provides a synthetic hypericin comprising hypericin as a mono-sodium salt in the form of a trihydrate.

A further object of the present invention provides a synthetic hypericin produced by a process comprising at least one of the following steps:

(a) photoconverting protohypericin to crude hypericin using micro-reactor equipped with a Light Emitting Diode (LED) light source either as batch or continuous mode;

(b) solubilizing crude hypericin in a solvent at a pre-precipitation temperature; filtering the treated hypericin while providing at least one cooling ramp to reach a post-precipitation temperature, wherein a precipitate is formed; washing and filtering the precipitate preferably with a washing solvent; and (c) treating crude hypericin with at least one salt forming reagent in a solvent at a pre-precipitation temperature; filtering the treated hypericin while providing at least one cooling ramp to reach a post-precipitation temperature, wherein a precipitate is formed; washing and filtering the precipitate preferably with a washing solvent, wherein the at least one step (a), (b) and (c) is followed by drying of the purified hypericin product with nitrogen, water vapor or air under vacuum.

Another object of the present invention provides a method of preparing a purified synthetic hypericin, the method comprising:

(a) photoconverting protohypericin to crude hypericin;

(b) treating the crude hypericin with a salt forming reagent in a solvent at a pre-precipitation temperature;

(c) filtering the crude hypericin from step (b) while providing at least one cooling ramp to reach a post-precipitation temperature, wherein a precipitate is formed;

(d) washing and filtering the precipitate from step (c) with a washing solvent; and (e) drying of the product of step (d) with nitrogen, water vapor or air under vacuum.

Yet another object of the present invention provides a method of preparing a purified synthetic hypericin wherein the irradiation is the result of exposure to standard light. Yet another object of the present invention provides a method of preparing a purified synthetic hypericin wherein the irradiation is the result of exposure to light. As light sources one can select suitable lamps such as a low or medium pressure mercury lamp. More preferred light sources are LED lights which can provide irradiation with a narrow desirable wavelength distribution.

Yet another object of the present invention provides a method of preparing a purified synthetic hypericin wherein the irradiation step is performed using a continuous flow reactor. In a preferred embodiment, the irradiation step is performed using a continuous flow microreactor.

Still another object of the present invention provides a method of preparing a purified synthetic hypericin resulting from LED irradiation, wherein the LED light has a wavelength between 350-700 nm.

Still another object of the present invention provides a process for manufacturing a purified synthetic hypericin.

Another object of the present invention provides a process for manufacturing purified synthetic hypericin wherein the synthetic hypericin yield is at least 30% of the dry product. In a preferred embodiment the synthetic hypericin yield is at least 50% of the dry product. In a more preferred embodiment the synthetic hypericin yield is at least 70% of the dry product. In a most preferred embodiment the synthetic hypericin yield is at least 75 to 100% of the dry product.

Another object of the present invention provides a process for manufacturing purified synthetic hypericin wherein the synthetic hypericin purity is at least 80% of the dry product. In a preferred embodiment the synthetic hypericin purity is at least 90% of the dry product. In a more preferred embodiment the synthetic hypericin purity is at least 95% of the dry product. In a most preferred embodiment the synthetic hypericin purity is at least 97% of the dry product.

BRIEF DESCRIPTION OF THE FIGURES

The novel features of this invention, as well as the invention itself, both as to its structure, reaction scheme and its operation, will be best understood from the accompanying drawings, taken in conjunction with the accompanying description, in which similar reference characters refer to similar parts, and in which.

DETAILED DESCRIPTION OF THE INVENTION

The system of the present invention contains one or more of the following steps:
(1) irradiation of protohypericin to crude hypericin; (2) purification of crude hypericin in methanol—method 1; (3) purification of crude hypericin in methanol with sodium bicarbonate—method 2; (4) drying of purified hypericin in the presence of air under reduced pressure; and (5) drying of purified hypericin in the presence of air and/or water vapor under reduced pressure.

Figure 2:
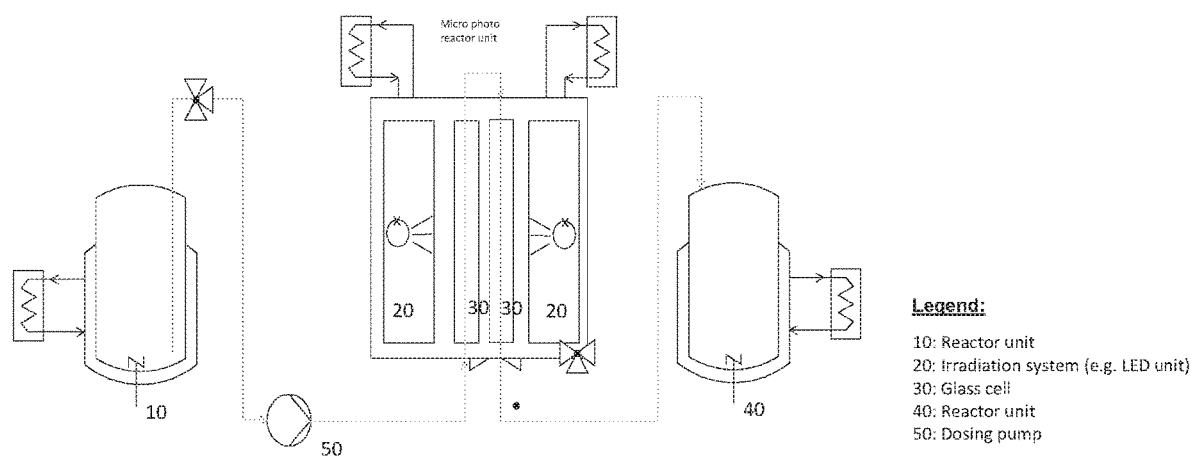
FIG. 2 depicts a process flow diagram for the manufacture of hypericin.

The Micro reactor system (FIG. 2) used for the irradiation step consists of 2 quartz glass laminar flow cells (size: 200 mm/120 mm/40 mm; gap: ID 80 μm; volume: 1.2 ml volume) with LED panels, having the preferred parameters of 54 W light energy at designated wavelength; panel size: 175 mm/100 mm,) as shown in FIG. 2.

Protohypericin was photoconverted to synthetic hypericin according to the methods presented in the Examples section. Briefly, protohypericin was mixed with acetone in a double-jacketed glass vessel equipped with a heating and cooling system. The resulting solution was filtered using a glass filter and washed with acetone. Additional acetone was added to the filtrate solution and which then was irradiated at the specified wavelength with LED panels. Irradiated solution was placed in a rotary evaporator for distillation followed by the addition of methanol for further distillation.

The distilled slurry was filtered and the solid was washed with a hexane/ethyl acetate mixture and dried. The resulting crude hypericin was mixed with methanol in a double-jacketed glass vessel equipped with a heating and cooling system and maintained at constant temperature. Next, the vessel was cooled and held at constant temperature while mixing. Crystallized hypericin was filtered and washed again with a hexane/ethyl acetate mixture and dried under nitrogen followed by vacuum drying. This drying process is also optimized for the generation of anhydrous hypericin salt.

Crude hypericin was mixed with methanol and sodium bicarbonate in a double-jacketed glass vessel equipped with a heating and cooling system and maintained at a constant pre-precipitation temperature and the resulting solution was filtered. Next, the contents were systematically cooled down to post-precipitation temperature allowing the product to be crystallized. Crystallized hypericin was filtered and washed again with a hexane/ethyl acetate mixture prior to drying under an air stream.

EXAMPLES

Synthetic Hypericin

Example 1: Irradiation Step of Protohypericin into Crude Hypericin

Protohypericin (45 g) was charged into a vessel followed by the addition of acetone and $NaHCO_3$. The suspension was heated to >40° C. The warm solution was filtered and washed with acetone.

Acetone was added to the protohypericin solution and cooled down to a temperature of 2° C. The solution was pumped through the irradiation unit at a flow rate of >15 ml/min and irradiated. The obtained hypericin solution was concentrated on a rotary evaporator at ambient temperature. Methanol was added, further distilled and concentrated. The final slurry was filtered and washed with a mixture containing hexane and ethyl acetate. The solid was dried under nitrogen followed by vacuum at room temperature. The resulting yield of crude hypericin was 27 g or roughly 60%.
Purity by HPLC [area %]: 98.12

Example 2: Purification of Hypericin (Method 1)

Crude hypericin (42 g) was suspended in methanol. The suspension was mixed, heated to pre-precipitation temperature >40° C. and filtered. The filtrate was cooled to post-precipitation temperature. The suspension containing purified hypericin solid was filtered and the filter cake was washed with a mixture of hexane and ethyl acetate in portions. The solid was dried in a nitrogen stream under vacuum for >48 hours. The obtained yield of pure hypericin was 40.1 g or roughly 95.5%.
Purity by HPLC [area %]: 97.95
Sodium content [wt %]: 3.8
Water content [wt %]: 0.96

Example 3: Purification of Hypericin (Method 2)

Crude hypericin (280.4 g) and methanol were charged in a vessel followed by the addition of sodium bicarbonate. The suspension was mixed and heated to pre-precipitation temperature >45° C. The warm solution was filtered. The filtrate was transferred to a glass reactor and cooled to post-precipitation temperature allowing the hypericin to crystallize. The crystallized hypericin was filtered and the filter cake was washed with a mixture of hexane and ethyl acetate in portions. The solid was dried in air stream under vacuum. The obtained yield of pure hypericin was 212.6 g or roughly 75.8%.
Purity by HPLC [area %]: 99.62
Sodium content [wt %]: 3.94
Water content [wt %]: 7.85

In order to utilize the purified hypericin as the active pharmaceutical ingredient for pharmaceutical drug applications, the present invention described in the examples above contains specific steps undertaken to reduce the residual solvents present in the final purified hypericin. Residual solvents are generally removed by drying the active pharmaceutical ingredient similar to the method of Example 2. These drying processes also remove water molecules from the active pharmaceutical ingredient resulting in the anhydrous status of the drug substance.

Chemical entities such as hypericin are not stable in their anhydrous forms and they tend to become hydrated over time even if they are protected from air by inert gas (such as nitrogen) replacement techniques. Therefore, solvent removal drying procedures in the presence of air and/or water under reduced pressure have been employed to remove residual solvents while preserving the hydrated stable form of hypericin.

Accordingly, the present invention provides methods to dry active pharmaceutical ingredients to reduce the residual solvents to an acceptable specification limits while keeping these drug substances in their most stable form.

Example 4: Drying of Purified Hypericin (Method 1)

The preferred method utilizes the same filtration unit used for the last step of the purified final crystallized hypericin from Example 3. After the product was filtered through the unit via the use of a vacuum pump, the unit was then allowed to intake a continuous air stream through disposable sterile 0.22 micron filter on one end of the unit while the vacuum was applied to the other end of the filtration device. The residual solvents from the product were removed by adjusting the temperature of the drying unit under vacuum. The temperature was set to be in the range between 0 to 100° C., preferably 20 to 70° C. and suitably 25 to 60° C. The vacuum was set in the range of 20 mbar to the atmospheric pressure, preferably 100 mbar to 700 mbar, suitably 200-600 mbar.

TABLE 1

Analytical Test Results for the hypericin batch produced under Examples 3 and 4

| Parameter Studied | Test Results |
|---|---|
| Extinction Coefficient [at 590 nm] Related substances [at 590 nm] | 51025 |
| Protohypericin [area %] | <0.05 |
| Impurity RRT 1.95 [area %] | 0.21 |
| Any other unspecified impurity [area %] | 0.17 |
| Total impurities [area %] | 0.38 |
| Hyperlcin purity [area %] [at 590 nm] | 99.62 |
| Hypericin Assay [wt. %] [at 590 nm] (anhydrous and solvent free substance) | 95.7 |
| Residual Solvents | |
| Acetone [ppm] | <100 |
| Ethyl Acetate [ppm] | 470 |
| Hexane [ppm] | 3110 |
| Methanol [ppm] | <100 |
| Piperidine [ppm] | 199 |
| Pyridine [ppm] | <100 |
| Total residual solvents [wt. %] | 0.38 |
| Water [wt. %] | 7.85 |
| Elemental impurities | |
| Sodium content [%] | 3.94 |
| Iron content [ppm] | <100 |
| Tin content [ppm] | <2000 |

Example 5: Drying of Purified Hypericin (Method 2)

An alternate method used vacuum oven to dry the drug substance in the presence of water vapor supplied through air intake or by placing a container of water in the oven. The residual solvents from the product were removed by adjusting the temperature of the drying unit under vacuum. The temperature was set to be in the range between 0 to 100° C., preferably 20 to 70° C. and suitably 25 to 60° C. The vacuum was set in the range of 20 mbar to the atmospheric pressure, preferably 100 mbar to 700 mbar, suitable 200-600 mbar Solvent Content (Ppm) Results of the Dried Sample

| Methanol | 2009 |
| Hexane | 1421 |
| Ethyl acetate | 5828 |

Composition of Purified Hypericin:

A systematic study was performed to determine the water content of the purified historical batch A along with recently manufactured batches B and C and their short term stability on the water content. The samples were taken from containers that were kept closed and sealed under nitrogen and containers that were kept open to the atmosphere for the indicated time and analyzed for the water content. Historical batch A had a water content of 9.3% and did not significantly increase after exposure to the air. The recently purified batches (B and C) started with low water content (<1%) and their values increased substantially suggesting that the hypericin molecule is hygroscopic and gets stabilized in its hydrated form. Historical batch A appeared to be stabilized at 9.3% which corresponds to the trihydrated form of the hypericin molecule (see below for calculation).

Figure 1:
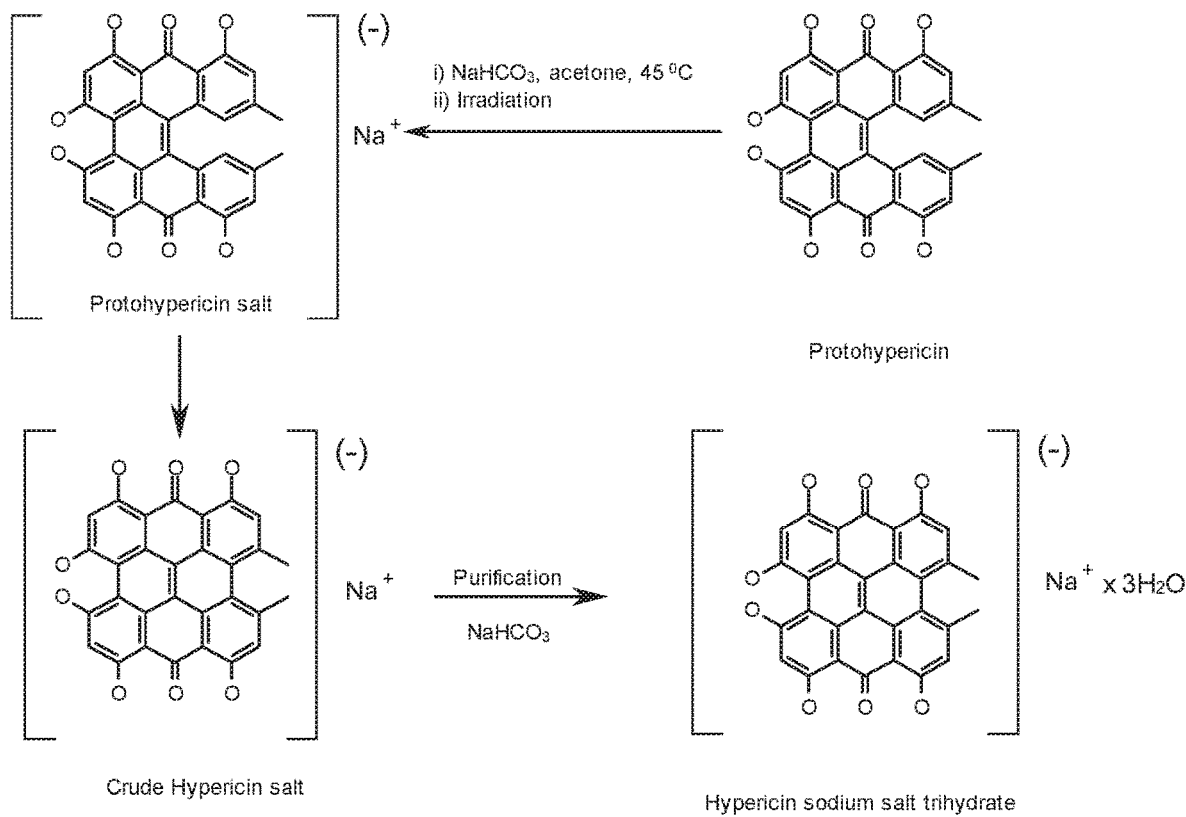
FIG. 1 depicts a reaction scheme for hypericin manufacture.

The sodium content of the manufactured batches was also monitored. During the manufacturing process, all protohypericin sub-batches were treated with sodium bicarbonate prior to the irradiation step (FIG. 1). However, manufacturing of a fully substituted sodium salt (monosodium) form of the hypericin was not possible by the pre-treatment of protohypericin with sodium bicarbonate alone. Further treatment of crude hypericin with sodium bicarbonate was necessary for the quantitative yield of hypericin monosodium salt. In order to ensure that the hypericin batch was manufactured as a monosodium salt, the final purification and crystallization of the crude hypericin was performed in the presence of methanol and sodium bicarbonate. The sodium content of the recently manufactured batch following the examples in 3 and 4 was found to be 3.94% supporting the manufacture of hypericin monosodium salt in its trihydrated form.

From the above observations, calculations were made to determine the molecular composition of the hypericin related forms. Examples were shown to manufacture anhydrous as well as hydrated forms of hypericin. Also included were the examples of manufacturing of monosodium salt as well as partially sodium substituted salt forms of hypericin. Therefore, the present invention directs methods/processes of choice to synthesize and purify hypericin in a variety of related forms such as the examples below:

Hypericin molecular weight $C_{30}H_{16}O_8$
Hypericin monosodium $C_{30}H_{15}O_8Na$
Hypericin monosodium trihydrate $C_{30}H_{15}O_8Na \cdot 3H_2O$
Hypericin monosodium trihydrate $C_{30}H_{15}O_8Na \cdot 3H_2O$ with a theoretical water content of 9.3% and sodium content of 3.96%

As used herein, the term "hypericin and hypericin derivative" means hypericin and its related molecular forms, or a combination thereof. It is clear to one of skill in the art that numerous insignificant modifications may be made to the chemical structure of hypericin and its related molecular forms and that many such modifications will not significantly alter the biological activity of the molecule. Hence, hypericin and its related molecular forms which have been insignificantly modified, such that the biological activity is not significantly altered, are included within the definition of an appropriate hypericin derivative. One of skill in the art will appreciate that they may use the methods taught herein to distinguish modified hypericin and its related molecular forms having insignificantly altered biological activity from those having significantly altered biological activity. The disclosure of U.S. Pat. Nos. 6,229,048 and 6,867,235 are herein incorporated by reference.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. For example, the precipitation and salt conversion experiments performed in methanol in the presence of sodium bicarbonate can be substituted by other solvents of 2 carbon to 5 carbon alcohol; ketones, preferably acetone, methyl ethyl ketone); alkyl acetates, preferably ethyl acetate for the solubilization step and by other salts forms (such as ammonium bicarbonate, potassium bicarbonate, calcium bicarbonate, magnesium bicarbonate. etc.) for the conversion to ammonium, potassium, calcium, magnesium salt etc. The final washing step can be performed with solvents selected from the group consisting of mixture of ethyl acetate/hexane (or pentane); ethers preferably methyl tertiary butyl ether (MTBE). One of skill in the art will therefore appreciate that they may use the methods taught herein to distinguish hypericin acid, hypericin sodium salt, ammonium salt, potassium salt, calcium salt, magnesium salt etc. and hypericin anhydrous and its hydrated forms (mono-, di- and trihydrated). It should therefore be understood that this invention is not limited to the particular embodiments described herein, but is intended to include all changes and modifications that are within the scope and spirit of the invention.

What is claimed is:

1. A method of preparing a purified synthetic hypericin, the method comprising:
   (a) photoconverting protohypericin to crude hypericin using a continuous flow micro-reactor;
   (b) treating the crude hypericin with at least one salt forming reagent in a solvent at a pre-precipitation temperature wherein the at least one salt forming reagent is selected from the group consisting of sodium bicarbonate, ammonium bicarbonate, potassium bicarbonate, calcium bicarbonate, and magnesium bicarbonate;
   (c) filtering the treated hypericin from step (b) while simultaneously providing at least one cooling ramp to reach a post-precipitation temperature, wherein a precipitate is formed;
   (d) washing and filtering the precipitate from step (c) with a washing solvent; and
   (e) drying of the product of step (d) with nitrogen, water vapor or air under vacuum.

2. The method claim 1, wherein the photoconverting is the result of exposure to a LED light at a wavelength between 350-700 nm.

3. The method of claim 1, wherein pre-precipitation temperature is greater than 40° C.

4. The method of claim 1, wherein the post-precipitation temperature is less than 40° C.

5. The method of claim 1, wherein the yield of the synthetic hypericin is equal to 30% of the dry product.

6. The method of claim 1, wherein the yield of the synthetic hypericin is equal to 50% of the dry product.

7. The method of claim 1, wherein the yield of the synthetic hypericin is equal to 70% of the dry product.

8. The method of claim 1, wherein the yield of the synthetic hypericin is equal to 75% of the dry product.

9. The method of claim 1, wherein the purity of the synthetic hypericin is equal to 30% of the dry product.

10. The method of claim 1, wherein the purity of the synthetic hypericin is equal to 50% of the dry product.

11. The method of claim 1, wherein the purity of the synthetic hypericin is equal to 70% of the dry product.

12. The method of claim 1, wherein the purity of the synthetic hypericin is equal to 75% of the dry product.

13. A method of preparing a purified synthetic hypericin, the method comprising:
   (a) treating a pure hypericin with at least one salt forming reagent in a solvent at a pre-precipitation temperature greater than 40° C.;
   (b) filtering the product from step (a) while simultaneously providing at least one cooling ramp to reach a post-precipitation temperature in a double-jacketed glass vessel equipped with a heating and cooling system, wherein a precipitate is formed;
   (c) washing and filtering the precipitate from step (b) with a washing solvent; and
   (d) drying of the product of step (c) with nitrogen, water vapor or air under vacuum.

* * * * *